US008042380B2

(12) United States Patent
Fujii et al.

(10) Patent No.: US 8,042,380 B2
(45) Date of Patent: Oct. 25, 2011

(54) GAS SENSOR

(75) Inventors: Yoshiyasu Fujii, Nagoya (JP); Hisaharu Nishio, Tokai (JP); Takayoshi Atsumi, Konan (JP); Naoki Yamada, Iwakura (JP)

(73) Assignee: NGK Spark Plug Co., Ltd., Nagoya-Shi (JP)

(*) Notice: Subject to any disclaimer, the term of this patent is extended or adjusted under 35 U.S.C. 154(b) by 507 days.

(21) Appl. No.: 12/208,473

(22) Filed: Sep. 11, 2008

(65) Prior Publication Data

US 2009/0071231 A1 Mar. 19, 2009

(30) Foreign Application Priority Data

Sep. 14, 2007 (JP) ................................ 2007-238976
Aug. 19, 2008 (JP) ................................ 2008-210348

(51) Int. Cl.
*G01N 7/00* (2006.01)

(52) U.S. Cl. ..................................................... 73/31.05

(58) Field of Classification Search .................. 73/31.05
See application file for complete search history.

(56) References Cited

U.S. PATENT DOCUMENTS

| | | | | |
|---|---|---|---|---|
| 6,395,159 | B2 * | 5/2002 | Matsuo et al. | 204/427 |
| 7,287,413 | B2 * | 10/2007 | Nishio et al. | 73/23.31 |
| 7,318,339 | B2 * | 1/2008 | Nishio et al. | 73/31.05 |
| 7,550,117 | B2 * | 6/2009 | Alward et al. | 422/177 |

FOREIGN PATENT DOCUMENTS

JP 2002-181765 A 6/2002

* cited by examiner

*Primary Examiner* — Hezron E Williams
*Assistant Examiner* — Rodney T Frank
(74) *Attorney, Agent, or Firm* — Leason Ellis LLP

(57) ABSTRACT

A gas sensor has a sensor element, extending axially, that detects a particular gas component in a gas under measurement, a metal housing causing the end of the sensor element to protrude farther than the end thereof to expose it to the gas under measurement and that surrounds the periphery of the sensor element and an outer tube disposed at the rear end inside the metal housing and a seal member that is disposed farther to the rear than the detection element and also inside the rear end of the outer tube, and that has formed therein a atmosphere-introduction hole passing therethrough in the axial direction, the gas sensor further having a crimped part, formed in the outer tube, for the purpose of holding the seal member a hollow-cylindrical member in contact with the inner peripheral surface of the atmosphere-introduction hole so as to oppose the crimped part, and a metal filter that joins to the hollow-cylindrical member at the rear end of the hollow-cylindrical member and also farther to the rear than the crimped part.

14 Claims, 8 Drawing Sheets

(a)
13 132 131
133 134 136 135

(b)
136 133 131
135

(a)

(b)

GAS SENSOR

CROSS-REFERENCE TO RELATED APPLICATION

The present application claims priority under 35 U.S.C. §119 to Japanese Patent Application Nos. 2007-238976 filed Sep. 14, 2007 and 2008-210348 filed Aug. 19, 2008. The content of the applications are incorporated herein by reference in their entireties

TECHNICAL FIELD

The present invention relates to a gas sensor that detects the concentration of a particular gas component in a gas to be measured, such as an exhaust gas.

BACKGROUND OF THE INVENTION

In the past, in a sensor for detecting the concentration of a particular gas component in a gas to be measured, such as an exhaust gas, as shown in Japanese Laid-Open Patent Application Publication 2002-181765 ("JP '765") a detection element is provided at the bottom part of the gas sensor, and a through hole is formed so as to pass through the center part of a seal member provided at the top part of the gas sensor in the axial direction, and further a ventilation filter is provided so as to block the through hole. This ventilation filter, in addition to introducing outside air into the inside of the gas sensor, is ventilating and water-repellant, so that even if the gas sensor is subjected to water, water is not introduced into the inside of the gas sensor. In this gas sensor, the sheet-like sealed ventilation filter is fitted over a hollow-cylindrical member and inserted into the through hole, so as to be held inside the through hole between the outer peripheral surface of the hollow-cylindrical member and the inner peripheral surface of the through hole, thereby blocking the through hole and achieving ventilation and waterproofing thereof.

An oxygen sensor such as in JP '765, however, uses PTFE or a fluorine-based resin or the like as a material, is susceptible to externally applied impacts, is damaged by externally applied force, and there is a risk of a hole forming in the ventilation filter. As a result, seepage of water content into the inside of the gas sensor from the outside can cause such problems as a decrease in the oxygen concentration detection output, or splitting of the detection element by being subjected to water, these being causes of gas sensor failure.

The present invention was made in view of the problems of the past, and provides a gas sensor having a high-strength ventilation filter while maintaining the ventilation and water repellency properties of the ventilation filter.

SUMMARY OF THE INVENTION

Given the above, a gas sensor of the present invention is a gas sensor provided with a detection element, extending in the axial direction, that detects a particular gas component in a gas under measurement, with a casing surrounding a periphery of the detection element and having a front end from which a front end of the detection element protrudes so that the front end of the detection element is exposed to the gas under measurement, and with a seal member disposed on a rear side with respect to the detection element and also inside a rear end of the casing, the seal member having a ventilation hole penetrating therethrough in the axial direction.

The gas sensor described above further has a crimped part of the casing which holds the seal member, and has a hollow-cylindrical member being in contact with an inner peripheral surface of the ventilation hole and opposed to the crimped part, and has at least one of a metal filter or a ceramic filter that joins to the hollow-cylindrical member at the base end of the hollow-cylindrical member and on a rear side with respect to the crimped part, and that at least covers the ventilation hole and has ventilating and water repellency properties.

The metallic filter or the ceramic filter has high strength compared with a resin filter of the past, and can reduce the amount of damage caused by an external force. The metallic filter or the ceramic filter is made of a porous material and has ventilating properties. Additionally, the metallic filter or the ceramic filter is treated for water repellency, by glazing on the surface and inside thereof (for example, by coating with a fluorine-based resin), and thus repels water.

Additionally, because the metallic filter or the ceramic filter is joined to the hollow-cylindrical member that makes contact with the inner peripheral surface of the through hole, the metallic filter or the ceramic filter can be easily disposed within the through hole.

In the case of mounting the metallic filter or the ceramic filter to the front end of the hollow-cylindrical member, there is a risk of water accumulating in the air gap between the metallic filter or the ceramic filter and the inner peripheral surface of the hollow-cylindrical member, thereby lowering the ventilating property, and further a risk of water seeping into the inside of the gas sensor, thereby resulting in failure of the detection element. However, by mounting the metallic filter or the ceramic filter to the rear end of the hollow-cylindrical member, the air gap between the metallic filter or the ceramic filter and the inner peripheral surface of the hollow-cylindrical member is reduced, thereby enabling prevention of the seepage of water into the inside of the gas sensor and damage to the detection element.

In the case, for example, of joining a metallic filter to a hollow-cylindrical member that is metallic, the joining method can be welding, simultaneous sintering, soldering, or brazing, and in the case, for example, of joining a ceramic filter and a hollow-cylindrical member that is metallic, or in the case of joining a metallic filter with a hollow-cylindrical member made of ceramic, the method of joining is preferably brazing.

Additionally, the hollow-cylindrical member is formed in the casing and is disposed so as to oppose the crimped part for holding the seal member. In the case of holding the seal member in the casing by crimping in this manner, by using crimping to hold the hollow-cylindrical member, it is not necessary to hold the hollow-cylindrical member within the ventilation hole of the seal member using a press fit or an adhesive or the like.

In the case of holding the hollow-cylindrical member by crimping of the casing, the metallic filter or the ceramic filter is disposed farther to the rear than the crimped part. By doing this, when the seal member is held in the casing by crimping, it is difficult for the metallic filter or the ceramic filter to be affected by the compression force from the seal member, making it possible to prevent deformation of the metallic filter or the ceramic filter.

Essentially, in the gas sensor of the present invention it is possible to prevent damage to the filter by externally applied impact and deformation of the filter by the force of crimping and, as a result, water content does not seep into the inside of the gas sensor from the outside by passing through the ventilation hole, thereby enabling prevention of a lowering of the oxygen concentration detection output and splitting and the like of the detection element by subjecting it to water.

Also, in the case in which the hollow-cylindrical member is crimped and held inside the seal member, a hollow-cylindrical member that is more difficult to deform than the amount of deformation of the seal member due to the crimping of the casing may be disposed. By doing this, when the seal member is held by crimping of the casing, even if the location on the seal member corresponding to the holding by crimping deforms by inward compression, the hollow-cylindrical member receives the compression force of the seal member, and it is therefore possible to prevent extreme deformation of the filter, which is provided so as to block the hollow-cylindrical member. Lowering of the ventilation of the filter is thus prevented, and it is possible to prevent a lowering of the detection accuracy. Also, the hollow-cylindrical member may be formed of a metal or a ceramic.

Additionally, a restricting part that restricts the movement of the hollow-cylindrical member along the axial direction may be provided on the outer peripheral surface of the hollow-cylindrical member. If this is done, it is possible to limit the position offset between the hollow-cylindrical member and the seal member.

Additionally, in a gas sensor of the present invention the metallic filter or the ceramic filter is preferably sheet-shaped. By the use of a sheet-shaped metallic filter or ceramic filter in this manner, it is possible to achieve good ventilation compared with a rod-shaped metallic filter or ceramic filter, while preventing damage by external forces.

Additionally, a gas sensor of the present invention is a gas sensor provided with a detection element, extending in the axial direction, that detects a particular gas component in a gas under measurement, a casing that causes the end of the detection element to protrude farther than the end thereof to expose it to the gas under measurement and that surrounds the periphery of the detection element, and a seal member that is disposed farther to the rear than the detection element and also inside the rear end of the casing, and that has formed therein a ventilation hole, from one outside surface toward another outside surface, the gas sensor comprising a crimped part, formed in the casing for the purpose of holding the seal member, and a metallic filter or a ceramic filter, in contact with the inner peripheral surface of the ventilation hole opposing the crimped part, that at least blocks the ventilation hole and has ventilating and water repellency properties, wherein the deformation amount of the metallic filter or the ceramic filter is at least 1% and no greater than 50% of a deformation amount of the crimped part.

The metallic filter or the ceramic filter has high strength compared to a resin filter of the past and can reduce the amount of damage caused by an external force. The metallic filter or the ceramic filter is made of a porous material and has ventilating properties. Additionally, the metallic filter or the ceramic filter is treated for water repellency on the surface and inside thereof (for example, by coating or glazing with a fluorine-based resin), and repels water.

Additionally, the metallic filter or the ceramic filter is disposed inside the through hole so as to oppose the crimped part for holding the seal member. In the case of holding the seal member in the casing by crimping in this manner, by using crimping to hold the hollow-cylindrical member, it is not necessary to hold the metallic filter or the ceramic filter within the through hole of the seal member using a press fit or an adhesive or the like.

Also, in the case in which the metallic filter or the ceramic filter is held by using crimping of the casing, the deformation amount of the metallic filter or the ceramic filter is at least 1% and no greater than 50% of a deformation amount of the crimped part. By doing this, when the seal member is held by crimping of the casing, it is possible to minimize the effect of the compression force of the seal member on the metallic filter or the ceramic filter, and possible to achieve sufficient ventilation in the metallic filter or the ceramic filter. Also, if 50% is exceeded, the ventilation of the metallic filter or the ceramic filter can be reduced, and at less than 1% it might not be possible to hold the metallic filter or the ceramic filter to the seal member by crimping. The "deformation by crimping" refers to the deformation distance (maximum distance) between before crimping and after crimping of the casing. Specifically, it is possible to obtain the deformation distance by measuring the distance, in the diameter direction, between a part of the casing that is not deformed between before and after crimping (a location having the same diameter as before the crimping part is crimped) and the crimping part. Also, the amount of deformation of the metallic filter or the ceramic filter refers to the deformation distance (maximum distance) between the metallic filter or the ceramic filter before and after crimping. Specifically, it is possible to obtain the deformation distance by measuring the distance, in the diameter direction, between a part of the filter that does not deform between before and after crimping (a location having the same diameter as before the crimping part is crimped) and a location at which filter deformation occurs.

Essentially, in the gas sensor of the present invention it is possible to prevent damage to the filter by externally applied impact and deformation of the filter by the force of crimping and, as a result, water content does not seep into the inside of the gas sensor from the outside by passing through the ventilation hole, thereby preventing of a lowering of the oxygen concentration detection output and splitting and the like of the detection element by subjecting it to water.

Additionally, a gas sensor of the present invention it is preferable that the ventilation hole extends in the axial direction from an outside end surface of the seal member toward a rear outside surface, and wherein the metallic filter or the ceramic filter comprises a hollow-cylindrical part linking the between the blocking part that blocks the ventilation hole and a blocking part, and that makes contact with the inner peripheral surface of the ventilation hole. By doing this, it is possible to provide a metallic filter or a ceramic filter in which the function of blocking part having ventilation and water repellency properties and the function of the hollow-cylindrical part that is held by crimping are separated. Also, although the blocking part and the hollow-cylindrical part may be joined and linked, it is preferable to form the blocking part and the hollow-cylindrical part integrally, thereby reducing the number of parts and reducing the assembly cost.

Additionally, in a gas sensor of the present invention it is preferable that the ventilation hole extends in the axial direction from an outside end surface of the seal member toward a rear outside surface, and that the metallic filter or the ceramic filter comprises a rod shape that fills the ventilation hole and covers the ventilation hole. By doing this, the metallic filter or the ceramic filter can be fabricated to be strong, thereby making it difficult for the metallic filter or the ceramic filter to deform by crimping.

Additionally, in a gas sensor of the present invention, it is preferable that the ventilation hole comprises an axial-direction communicating hole that extends rearward from a front end surface of the seal member in the axial direction, and a radial-direction communicating hole that extends from an outside surface of the seal member up until the axial-direction communicating hole, whereby there is communication from the end outside surface of the seal member to the outside surface of the seal member, and wherein the metallic filter or the ceramic filter blocks the radial-direction communicating hole and is in contact with the inner peripheral surface of the axial-direction communicating hole. By doing this, the metallic filter or the ceramic filter has ventilation and water-repellency properties at the location at which the radial-direction communicating hole is blocked thereby, and is held by crimping at other locations, thereby providing a metallic filter or a ceramic filter that has separated functions.

Additionally, in a gas sensor of the present invention, it is preferable that the hollow-cylindrical member is ceramic and that an overcoating layer be formed on at least the side surface thereof.

In the case in which the hollow-cylindrical member is ceramic, although there is vertical unevenness in the side surface, by providing an overcoating layer on the side surface the vertical unevenness is eliminated and smoothness is achieved, so that the inner peripheral surface of the seal member is not damaged, and holding is done with a high degree of air-tightness between the hollow-cylindrical member and the seal member.

It is preferable that the overcoating (glaze) layer thickness be between 20 and 1000 μm (and particularly preferable that it be 50 μm). The reason that the overcoating layer is at least 20 μm is that although a thinner layer results in an increase in the strength of the hollow-cylindrical member, there are cases in which missed portions occur on the side surface of the hollow-cylindrical member, and it is not possible to form a uniform overcoating layer. Also, keeping the thickness of the overcoating layer within 100 μm is done because there are cases in which excessive layer thickness results in reduced hollow-cylindrical member strength because of the effect of the shrinkage ratio.

DETAILED DESCRIPTION OF THE INVENTION

Figure 1:
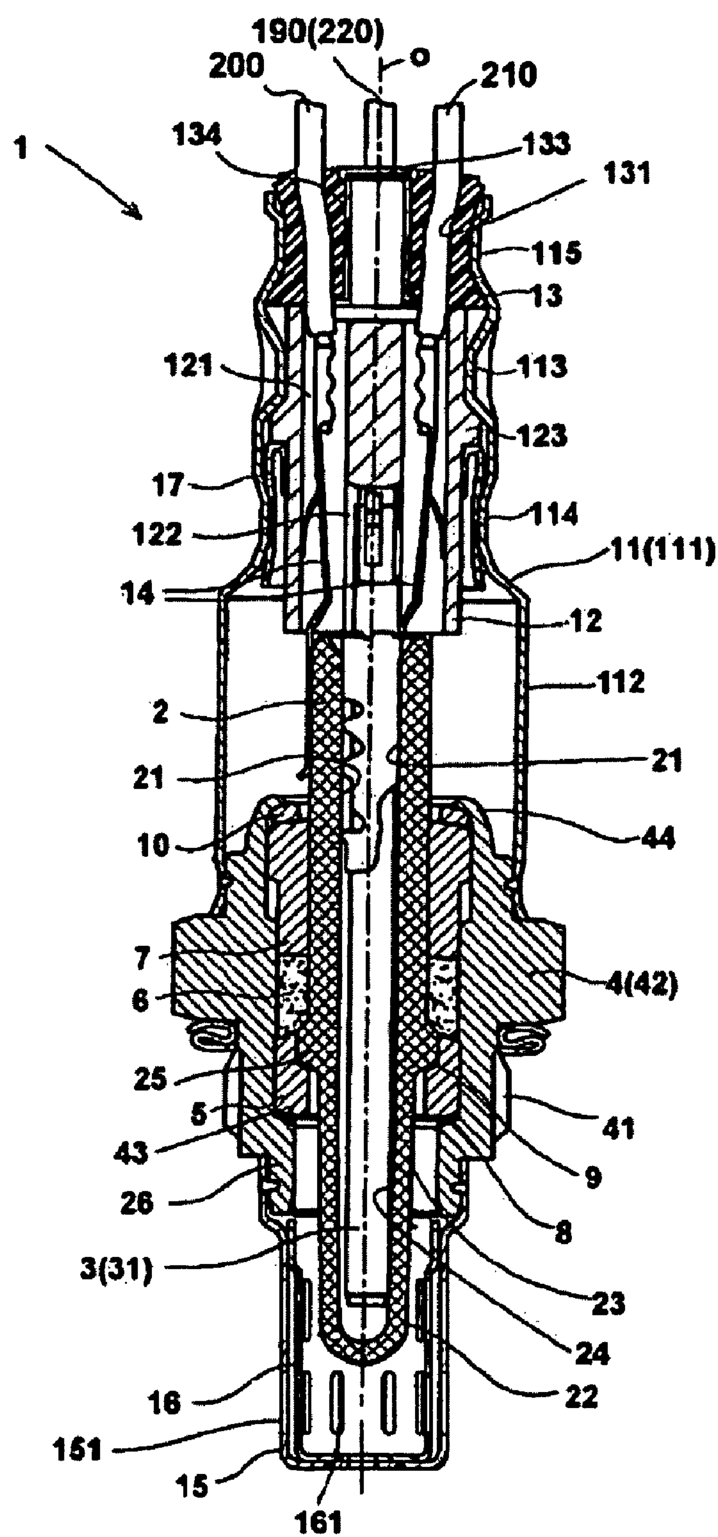
FIG. 1 An overall cross-sectional view of the gas sensor according to the Invention.

A gas sensor that is an embodiment to which the present invention has been applied will now be described, along with related drawings. In this embodiment, the description is of a gas sensor (oxygen sensor), mounted in an exhaust pipe of a vehicle that detects the concentration of oxygen in exhaust gas. FIG. 1 is a cross-sectional view showing the overall configuration of the gas sensor 1 of this embodiment.

As shown in FIG. 1, the gas sensor 1 has a sensor element 2 forming a hollow cylindrical shape with a bottom, with the end thereof closed, a ceramic heater 3 that is inserted into the bottomed hole 21 of the sensor element 2, and a metal housing 4 that holds the sensor element 2 therein. In this embodiment, of the directions along the axis of the sensor element 2 shown in FIG. 1, the side toward the end part (closed side, at the bottom in the drawing) that is exposed to the gas under measurement (exhaust gas) will be referred to as the "front end," and the side facing the oppose side (top in the drawing) will be referred to as the "rear end."

The sensor element 2 is a solid-state electrolyte having oxygen-ion conductivity and having as its main component partially stabilized zirconia in a solid solution of yttria as a stabilizing agent, and has a detection part 22 at its front end. Of the detection part 22, on the inner surface of the bottomed hole 21, an internal electrode 24 of platinum or a platinum alloy is formed porously to cover substantially the entire surface of the detection part 22, and an outer electrode 23 is formed porously in the same manner as the inner electrode 24. A mating flange part 25 that protrudes outwardly in the radial direction is provided at substantially the center position of the sensor element 2 in the axial direction. The ceramic heater 3 has heating part 31 that is rod-shaped and that has a resistive heating element therein. The ceramic heater 3 is electrically powered via the heater lead wires 190, 220, to be described later, so that the heating part 31 generates heat and heats the sensor element 2 so as to activate the sensor element 2.

The metal housing 4 has a threaded part 41 for the purpose of mounting the gas sensor 1 to a mounting part of the exhaust pipe, and a tool mating part 42 for the purpose of engaging with a tool at the time of mounting to the mounting part of the exhaust pipe. The metal housing 4 is provided with a housing-side step 43 protruding inwardly in the radial direction on the front side inner periphery, and a support member 5 is held by the housing-side step 43 via packing 8. In the sensor element 2, by the mating flange part 25 being supported on the support member 5 via the packing 9, it is supported by the metal housing 4. A filler 6 is disposed between the inner surface of the metal housing 4 at the rear end of the support member 5 and the outer surface of the sensor element 2, and a sleeve 7 and an annular ring 10 are successively inserted coaxially at the rear end of the filler 6. The housing-side rear end part 44 of the metal housing 4 crimped inwardly and forwardly so as to hold the sensor element 2 to the metal housing 4. In the gas sensor 1, the structure is such that, by crimping the housing-side rear end part 44, the filler 6 is compressed and filled via the sleeve 7, the result being that the sensor element 2 is held inside the hollow-cylindrical metal housing 4 in an air-tight condition.

An outer cover 15 is joined to the front end part 26 of the metal housing 4. The outer cover 15 has a bottomed hollow-cylindrical shape that covers the area around the detection part 22 of the sensor element 2 that protrudes from the metal housing 4. Additionally, an inner cover 16 is formed on the inside of the outer cover 15. In the same manner as the outer cover 15, the inner cover 16 has a bottomed hollow-cylindrical shape that covers the detection part 22 of the sensor element 2. The outer cover 15 and the inner cover 16 have formed in them ventilation holes 151, 161 for the purpose of exposing the sensor element 2 to the exhaust gas.

The front end of an outer tube 11 is joined to the rear end of the metal housing 4. An outer tube stepped part 111 is formed in the outer tube 11 at substantially the center position in the axial direction, an outer tube front end body part 112 is positioned on a front side with respect to the outer tube stepped part 111, and the outer tube rear end body part 113 is positioned on a rear side with respect to the outer tube stepped part 111. Of these, a first crimping part 114 for the purpose of holding the holding member 17 described below, and a second crimping part 115 for the purpose of holding the seal member 13 described below are formed on the outer tube rear end body part 113.

A separator 12 is disposed, via the holding member 17, inside the outer tube rear end body part 113 of the seal member 13, The separator 12 is formed so that the separator lead wire insertion hole 121 passes from the front end up to the rear end for the purpose of inserting the element lead wires 200, 210 and the heater lead wires 190, 220. A bottomed holding hole 122 that is open at the end surface thereof is formed in the axial direction in the separator 12. The rear end part of the ceramic heater 3 is inserted into the holding hole 122, and by the rear end surface of the ceramic heater 3 making contact with the bottom surface of the holding hole 122, the ceramic heater 3 is positioned in the axial direction with respect to the separator 12. The separator 12 has a separator flange part 123 provided to extend to the circumferential periphery.

The element lead wires 200, 210 and the heater lead wires 190, 220 pass through the separator lead wire insertion holes 121 of the separator 12 and the lead wire insertion hole 131 of the seal member 13 and extend toward the outside from the inside of the outer tube 11. The four lead wires 190, 200, 210, and 220 are connected outside to a connector that is not illustrated, and pass through the connector so as to make signal inputs and outputs with each lead wire 190, 200, 210, and 220 with an external device such as an ECU.

The lead wires 190, 200, 210 and 220, although not illustrated in detail, have structures in which the conductors are covered by a resin insulating covering, and the rear ends of the conductors are connected to connector terminals provided in the connector. The front end of the conductor of the element lead wire 200 is crimped with the rear end part of the terminal fixture 14 that is fitted over the outer surface of the sensor element 2, and the front end of the conductor of the element lead wire 210 is crimped with the rear end part of the terminal fixture 15 that is press fit into the inner surface of the sensor element 2. By doing this, the element lead wire 200 is electrically connected to the outer electrode 23 of the sensor element 2, and the element lead wire 210 is electrically connected to the inner electrode 24. The front ends of the conductors of the heater lead wires 190 and 220 are each respectively connected to the pair of heater terminal fixtures joined with the resistive heating element of the ceramic heater 3.

Figure 2:
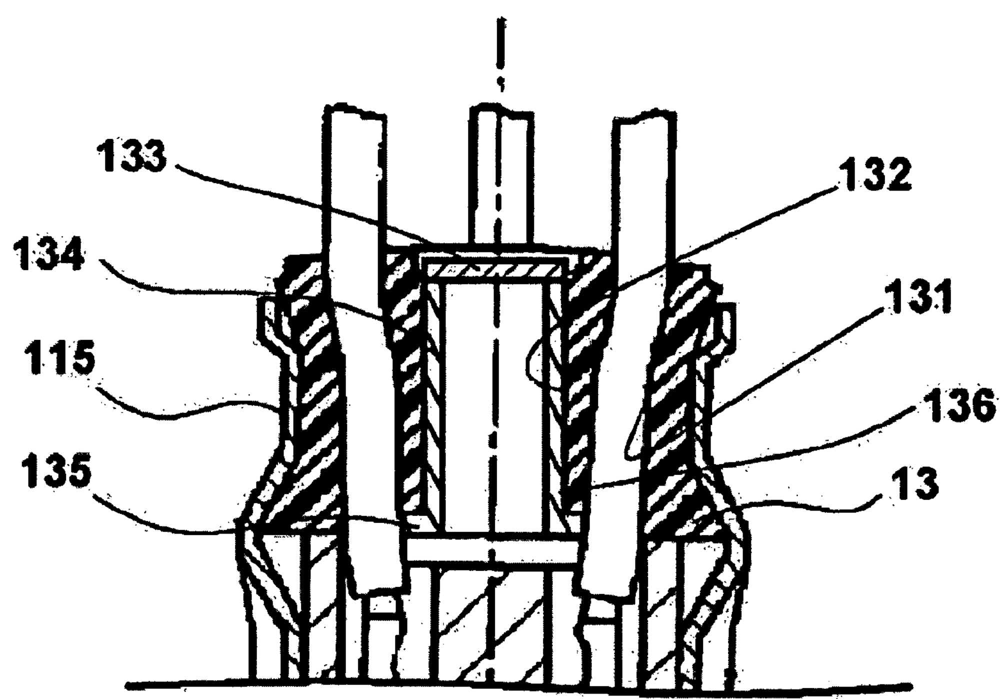
FIG. 2 A partial cross-sectional view of the gas sensor according to an embodiment.

Next, the seal member 13, which is the main part of the present invention, will be described in detail. As shown in FIG. 1 and FIG. 2, for the purpose of inserting the two element lead wires 200, 210 that electrically connect the sensor element 2, and the two heater lead wires 190, 220 that electrically connect the ceramic heater 3, four lead wire insertion holes 131 are formed in the seal member 13, which is disposed inside the rear end of the outer tube 11, so as to communicate from the front end to the rear end. Additionally, an atmosphere-introduction hole 132 is formed at substantially the center of the seal member 13, from the front end toward the rear end. The seal member 13 is made of fluoride rubber or the like.

A metallic filter 133 is disposed inside the atmosphere-introduction hole 132 so as to block the atmosphere-introduction hole 132. The metallic filter 133 is made of a metallic material such as stainless steel, a copper or copper alloy, a nickel or low alloy steel, or aluminum or the like, which has been treated to impart water repellency, and has ventilation and water repellency properties. By using the metallic filter 133 in this manner, there is no breakage even in an external impact is received.

Additionally, the metallic filter 133 is joined to the rear end of a hollow-cylindrical member 134 that makes contact with the inner peripheral surface of the atmosphere-introduction hole 132. Because the metallic filter 133 is joined to the rear end of the hollow-cylindrical member 134 in this manner, not only is it possible to easily dispose the metallic filter 133 in the atmosphere-introduction hole 132, but also there is no formation of an air gap between the metallic filter 133 and the hollow-cylindrical member 134, so that there is no seepage of water content into the gas sensor.

The hollow-cylindrical member 134 is disposed so as to oppose the crimped part 115. By doing this, in the case of holding the seal member 13 by crimping of the outer tube 11, it is possible to use the crimping to hold the hollow-cylindrical member 134.

Additionally, the hollow-cylindrical member 134 is formed from a metallic material having a strength that is greater than that of the seal member 13, such as stainless steel, a copper or copper alloy, a nickel or low alloy steel, or aluminum or the like. In contrast, the seal member 13 is formed from fluoride rubber. As a result, in the case in which the second crimping part 115 is formed, even if the location on the seal member 13 that corresponds to the second crimping part 115 deforms inwardly by compression, the hollow-cylindrical member 134 receives the compression force of the seal member 13, and it is possible to prevent extreme deformation of the metallic filter 133 that is provided so as to block the hollow-cylindrical member 134. Thus, a lowering of the ventilation properties of the metallic filter is prevented, as is a lowering of the detection accuracy of the gas sensor 1.

In the case in which the hollow-cylindrical member 134 is held by the crimping of the outer tube 11, the metallic filter 133 is disposed farther to the rear than the crimping part 115. By doing this, it becomes difficult for the metallic filter 133 to be affected by the compression force due to crimping, and it is possible to limit the deformation of the metallic filter 133.

Thus, by disposing the metallic filter 133 using the above-noted configuration, it is possible to prevent damage caused by externally applied impact, and also to prevent deformation of the metallic filter 133 by the crimping of the outer tube 11. As a result, there is no seepage of water content from the outside into the inside of the gas sensor 1 via the atmosphere-introduction hole 132, and it is possible to limit the lowering of the oxygen detection output and splitting and the like of the sensor element 2 caused by subjecting it to water.

The metallic filter 133 is formed in the shape of a sheet. By doing this, it is possible to maintain good ventilation properties in comparison with a rod-shaped metallic filter, while limiting damage from external force.

The hollow-cylindrical member 134 is provided in a hollow-cylindrical part 136 that makes contact with the inner peripheral surface of the atmosphere-introduction hole 132 and at the front end of the hollow-cylindrical part 136, and has a restricting part 135 that mates with a depressed part formed in the end surface of the seal member 13. By causing the hollow-cylindrical member 134 that is blocked by the metallic filter 133 to make contact with the inner peripheral part of the atmosphere-introduction hole 132 in this manner, it is possible to easily dispose the sheet-shaped metallic filter 133 in the atmosphere-introduction hole 132. Additionally, by providing a restricting part 135 that restricts the movement of the hollow-cylindrical member 134 along the axial direction, it is possible to limit the position offset between the hollow-cylindrical member 134 and the seal member 13.

Next, a method of manufacturing the gas sensor 1 of this embodiment will be described in detail. First, after forming pellets having yttria of 5 mol % added to zirconia, a bottomed cylinder having a closed end is formed and is sintered in an electrical oven at a temperature of 1400° C. to 1600° C., to obtain a solid-state electrolyte. Next, vapor deposition or chemical plating is used to provide the outer electrode 23 made of platinum on the outer peripheral surface of the solid-state electrolyte. In the same manner, vapor deposition or chemical plating is used to form the inner electrode 24 on the inside surface of the solid-state electrolyte, thereby obtaining the sensor element 2.

Continuing, the outer cover 15 is fit over the front end part 26 of the metal housing 4 into which the inside 16 is inserted, and laser welding is done around the entire periphery. Then the packing 8, the support member 5, the packing 9, the sensor element 2, the filler 6, and the sleeve 7 are sequentially inserted into the metal housing 4, and housing-side rear end part 44 of the metal housing 4 is crimped to prepare the sensor lower intermediate part.

The element lead wires 200 and 210 are each joined to the terminal fixtures 14, 14, and the heater lead wires 190 and 220 are joined to the heater terminal fixture of the ceramic heater 3. Then, with the ceramic heater 3 positioned inside the terminal fixtures 14, the lead wires 190, 200, 210, and 220 are inserted through each of the separator lead wire insertion holes 121 of the separator 12.

Figure 3:
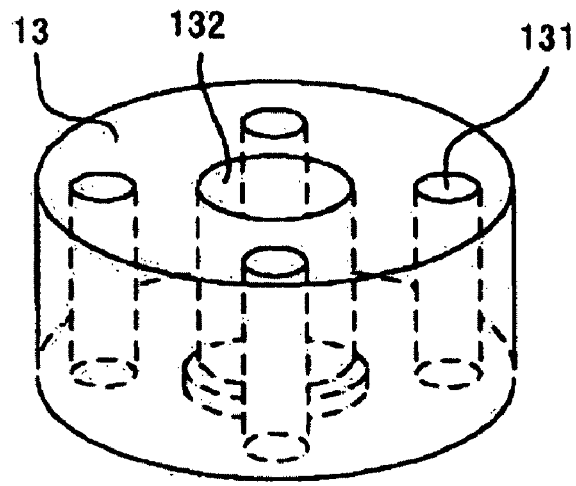
FIG. 3(*a*) is an exploded view of the region near the seal member in the above embodiment, and (*b*) is an assembly drawing of the region near the seal member before crimping in the above embodiment.
Figure 3:
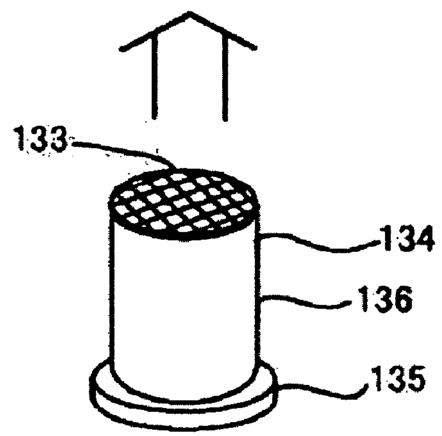
Figure 3:
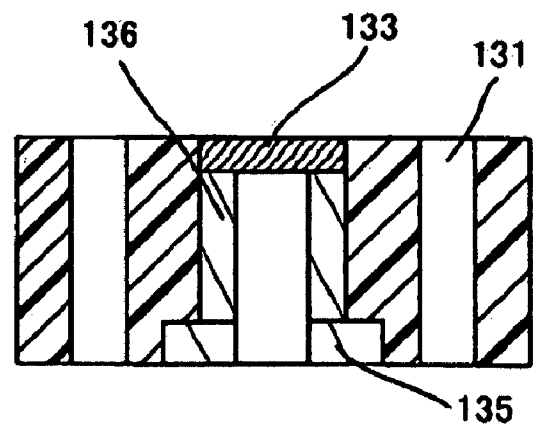

Continuing, the hollow-cylindrical part 136 and the restricting part 135 of the hollow-cylindrical member 134 are welded, and further the metallic filter 133 is welded and held at the rear end of the hollow-cylindrical member 134. As shown in FIG. 3(*a*), the hollow-cylindrical member 134 to which the metallic filter 133 is welded is inserted into the seal member 13. FIG. 3(*b*) is an assembly drawing showing the hollow-cylindrical member 134 before being inserted into the seal member 13 and held by crimping. The seal member 13 with which the hollow-cylindrical member 134 is integrated is then disposed at the rear end of the outer tube 11.

Next, with the lead wires 190, 200, 210, and 220 inserted through the lead wire insertion holes 131 of the seal member 13, the separator 12 is disposed inside the outer tube 11 so that the rear end surface makes contact with the front end surface of the seal member 13.

The outer tube 11 of the sensor upper intermediate part is inserted into the rear end side of the metal housing 4, and the part of overlapping between the outer tube 11 and the metal housing 4 is crimped. A first crimping part 114 is formed to crimp the outer tube 11 so as to hold the holding member 17. Additionally, the outer tube 11 is crimped so as to hold the seal member 13, thereby forming the second crimped part 115. The crimping is done by eight-direction round crimping. When this is done, the hollow-cylindrical member 134 is held inside the atmosphere-introduction hole 132 of the seal member 13 by the crimping of the outer tube 11 that holds the seal member 13. In the case of holding the seal member 13 in the outer tube 11 by crimping in this manner, by holding the hollow-cylindrical member 134 by using crimping, it is not necessary to do separate press fitting or use an adhesive or the like.

The part of overlapping between the outer tube 11 and the metal housing 4 is laser-welded so as to fix the outer tube 11 to the metal housing 4, thereby completing the gas sensor 1.

Figure 4:
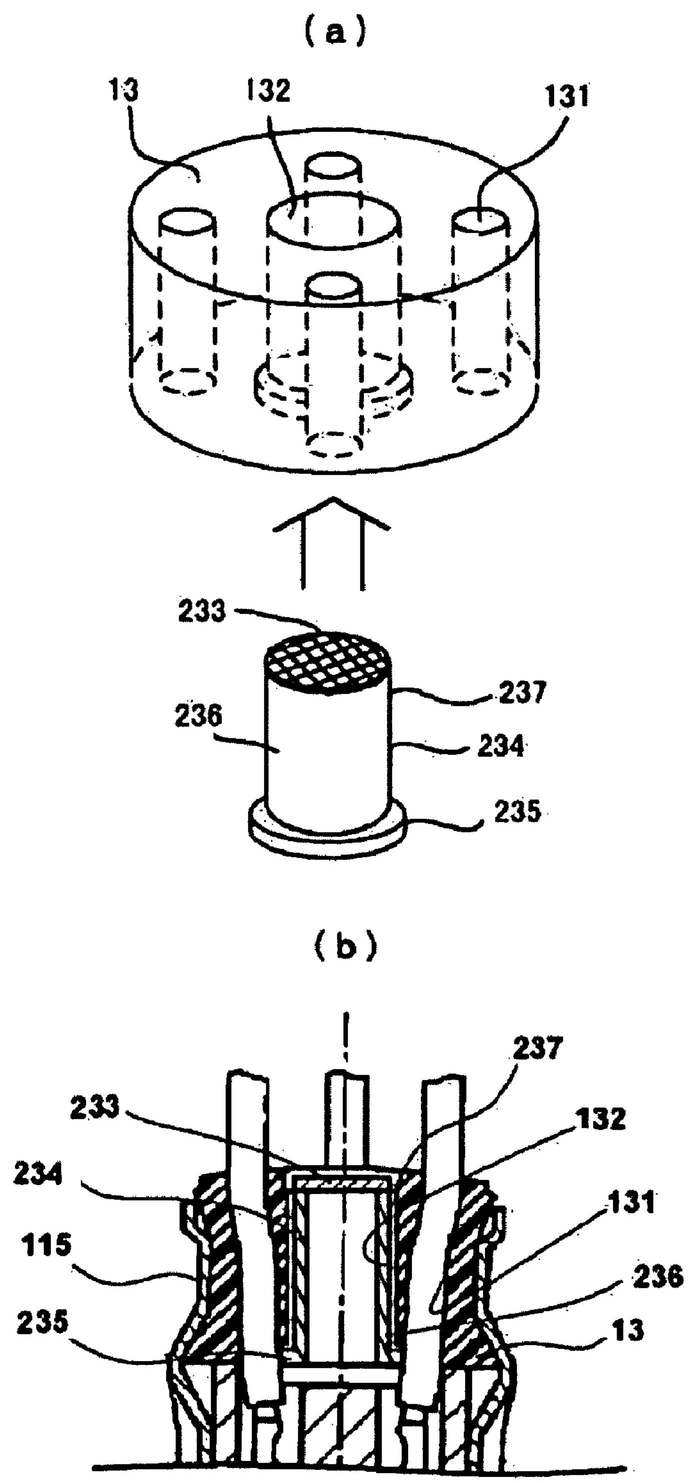
FIG. 4(*a*) is an exploded view of the region near the seal member in another embodiment, and (*b*) is a partial cross-sectional view of the region near the seal member this embodiment.

The next embodiment will be described using FIG. 4. In the previous embodiment, a metallic material was used in the hollow-cylindrical member 134 and a metallic filter 133 was used that blocks the hollow-cylindrical member 134. In this embodiment, however, a ceramic filter capable of withstanding the crimping force from the external member 11 is used in the hollow-cylindrical member 134, and a ceramic filter 233 which has been treated for water repellency is used in place of the metallic filter 133. Also, in this description, the description is of the region of the seal member 13, which differs from the above embodiment, and the descriptions of the other parts are omitted. FIG. 4(*a*) is an exploded view the condition in which the hollow-cylindrical member 234, to the front and rear ends of which the ceramic filter 233 is joined, is inserted into the seal member 13. FIG. 4(*b*) is a partial exploded view of the insertion of the hollow-cylindrical member 234 into the seal member 13 and holding of the seal member 13 by the crimping of the outer tube 11.

As shown in FIG. 4(*a*) and FIG. 4(*b*), in the second embodiment the ceramic filter 233 and the hollow-cylindrical member 234 are disposed inside the atmosphere-introduction hole 132 of the seal member 13. Of these, the ceramic filter 233 is made of a ceramic material such as alumina, silicon carbonate, or zirconia or the like, and has ventilation and water-repellency properties. Additionally, the hollow-cylindrical member 234 is attached to the front end of the ceramic filter 233 by simultaneous sintering. The hollow-cylindrical member 234 is made from a ceramic materials such as alumina, silicon carbonate, or zirconia or the like, and has a hollow-cylindrical part 236 that makes contact with the inner peripheral surface of the atmosphere-introduction hole 132 and a restricting part 235 that mates with a depression provided in the front end face of the seal member.

By using the ceramic filter 233 in this manner, there is no breakage even if an external impact is received.

Additionally, because the ceramic filter 233 is joined to the rear end of the hollow-cylindrical member 234 that makes contact with the inner peripheral surface of the atmosphere-introduction hole 132, it is easy to dispose the ceramic filter 233 in the atmosphere-introduction hole 132.

The hollow-cylindrical member 234 is disposed so as to oppose the crimping part 115. By doing this, it is possible to make it difficult for the ceramic filter 233 to be affected by compression force by crimping, thereby enabling limiting of the deformation of the ceramic filter 233.

Therefore, by disposing the ceramic filter 233 in the above-described configuration, it is possible to limit damage by externally applied impact and to limit deformation of the ceramic filter by the crimping of the outer tube 11. As a result, water content does not seep from the outside into the inside of the gas sensor 1 by passing through the atmosphere-introduction hole 132, thereby limiting the lowering of the oxygen concentration detection output and splitting of the sensor element 2 by being subjected to water.

Additionally, an overcoating layer 237 (or glaze layer) is formed on the side surface of the hollow-cylindrical part 236. By forming an overcoating layer 237 on the side surface of the hollow-cylindrical part 236 in this manner, vertical unevenness in the side surface of the hollow-cylindrical part of the hollow-cylindrical member 234 is eliminated and smoothness is achieved, so that the inner peripheral surface of the seal member 13 is not damaged, and holding is done with a high degree of air-tightness between the hollow-cylindrical member 234 and the seal member 13. The thickness of the overcoating layer 237 is preferably 50 μm.

Figure 5:
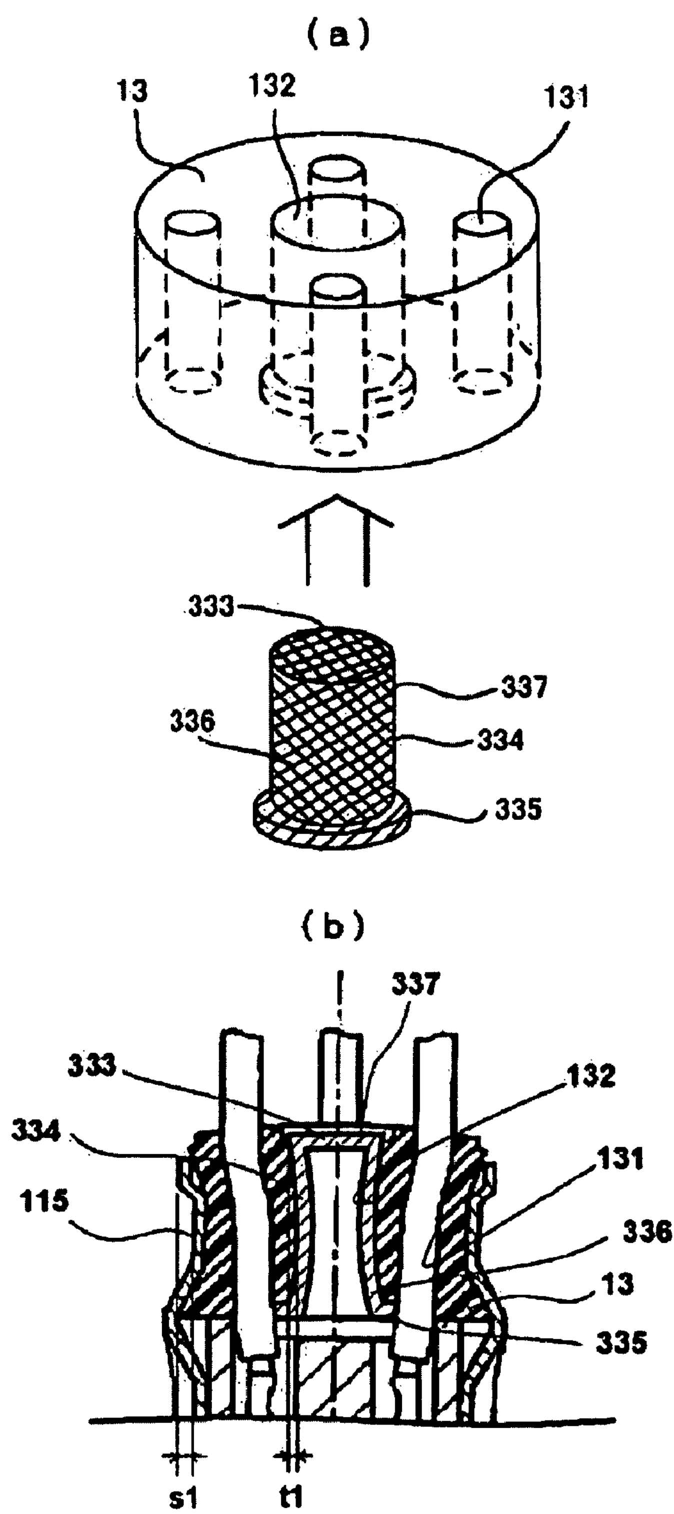
FIG. 5(*a*) is an exploded view of the region near the seal member in the further embodiment, and (*b*) is partial cross-sectional view of the region near the seal member in this third embodiment.

The next embodiment will be described, using FIGS. 5(*a*) and (*b*). In contrast to the other embodiments, in which the metallic filter 133 and the hollow-cylindrical member 234 were separate members, in this embodiment, as shown in FIG. 5, a metallic filter 333 that has been treated for water repellency and a hollow-cylindrical member 334 are integrally formed. The region of the seal member 13, which differs from the other embodiments will be described, with the descriptions of other parts being omitted or simplified. FIG. 5(*a*) is an exploded view of the condition in which a metallic filter 337, in which the metallic filter 333 and the hollow-cylindrical member 334 are integrally formed, is inserted into the seal member 13. FIG. 5(*b*) is a partial cross-sectional view in which the metallic filter 337 is inserted into the seal member 13 and the seal member 13 is held by crimping the outer tube 11.

As shown in FIG. 5, the metallic filter 337 is disposed inside the atmosphere-introduction hole 132 at substantially the center of the seal member 13. The metallic filter 337 has a blocking part 333 that blocks the atmosphere-introduction hole 132 and a hollow-cylindrical part 334 that connects to the blocking part 333. Additionally, a restricting part 335 that mates with a depression provided in the front end face of the seal member is provided at the front end of the hollow-cylindrical part 334.

By using the metallic filter 337 in this manner, it is possible to reduce damage caused by external forces.

Additionally, because the metallic filter 337 is disposed inside the atmosphere-introduction hole 132 so as to oppose the crimped part 115 formed in the outer tube 11, it is not necessary to press fitting or adhesives or the like to hold the metallic filter 337 in the atmosphere-introduction hole 132 of the seal member 13.

In this embodiment, the deformation amount t1 of the ventilation filter 337 is 10% of the deformation amount s1 of the crimped part 115. By the amount of deformation t1 of the metallic filter 337 being at least 1% but no more than 50% of the deformation amount s1 of the crimped part 115, when the seal member 13 is held by crimping of the outer hollow-cylindrical tube 11, it is possible to minimize the effect on the metallic filter 337 of the compression force of the seal member 13, and possible to achieve sufficient ventilation of the metallic filter 337.

Also, it is possible to make the metallic filter 337 separate the functions of the blocking part 333 that has ventilation and water repellency properties and the hollow-cylindrical part 334 that is held by the crimped part. Also, by using a metallic filter 337 that integrates the metallic filter 333 and the hollow-cylindrical member 334, it is possible to reduce the number of assembled parts and to reduce the assembly cost. The integrally formed metallic filter 337 may be made of a metal material, such as high-strength stainless steel, copper or a copper alloy, nickel, a low alloy steel, or aluminum or the like.

Figure 6:
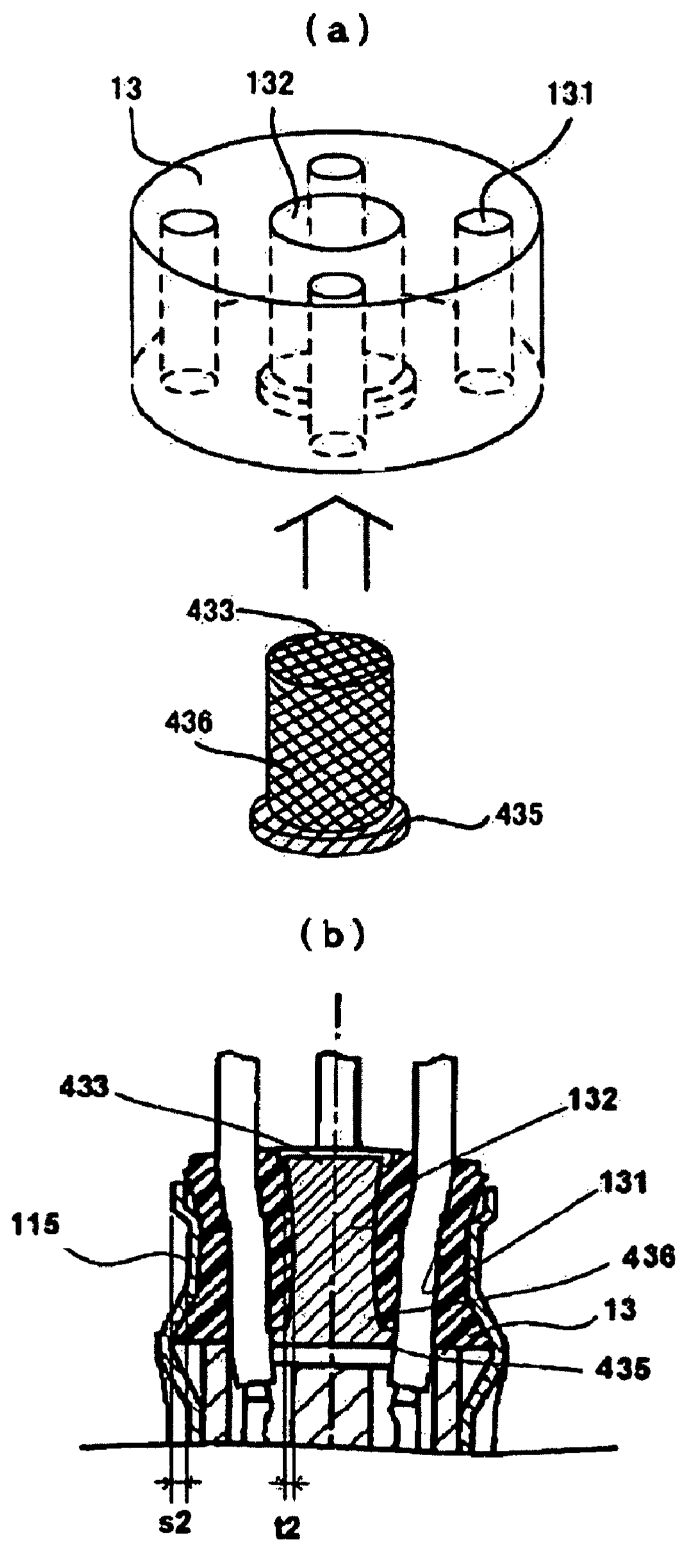
FIG. 6(*a*) is an exploded view of the region near the seal member in an embodiment, and (*b*) is a partial cross-sectional view of the region near the seal member in this embodiment.

Another embodiment will be described, using FIG. 6. In contrast to the above embodiments, in which a sheet-shaped metallic filter 133 was disposed inside the atmosphere-introduction hole 132 of the seal member 13 using a hollow-cylindrical member 134, in this embodiment, as shown in FIGS. 6(*a*) and (*b*), without using the hollow-cylindrical member 134, a rod-shaped metallic filter 433 that is treated for water-repellency is disposed inside the atmosphere-introduction hole 132 of the seal member 13. The description is of the region of the seal member 13, which differs from the above embodiments, and descriptions of other parts are omitted or simplified. FIG. 6(*a*) is an exploded view when the rod-shaped metallic filter 433 is inserted into the seal member 13, and FIG. 6(*b*) is a partial cross-sectional view showing the rod-shaped metallic filter 433 inserted into the seal member 13 and the seal member 13 held by crimping of the outer tube 11.

As shown in FIG. 6, the metallic filter 433 is disposed inside the atmosphere-introduction hole 132 that is in substantially the center of the seal member 13. The metallic filter 433 is provided at a hollow-cylindrical part 436 that makes contact with the inner peripheral surface of the atmosphere-introduction hole 132 and at the front end of the hollow-cylindrical part, and has a restricting part 435 that mates with a depression provided in the front end face of the seal member. By using a rod-shaped metallic filter 433 such as this, the number of assembled parts is reduced, and it is possible to lower the assembly cost. Additionally, because a rod-shaped metallic filter 433 is used, it is possible to be able to withstand crimping from the outer tube 11 while maintaining ventilation. The metallic filter 433 may be made from a metallic material such as high-strength stainless steel, copper or a copper alloy, nickel, low alloy steel, or aluminum or the like.

In this embodiment, the deformation amount t2 of the metallic filter 433 is 2% of the deformation amount s2 of the crimped part 115. By making the deformation amount t2 of the metallic filter 433 be at least 1% but no greater than 50% of the deformation amount s2 of the crimped part 115, when the seal member 13 is held by crimping of the outer tube 11, it is possible to limit the effect on the metallic filter 433 of the compression force from the seal member 13, and possible to achieve sufficient ventilation in the metallic filter 433.

Figure 7:
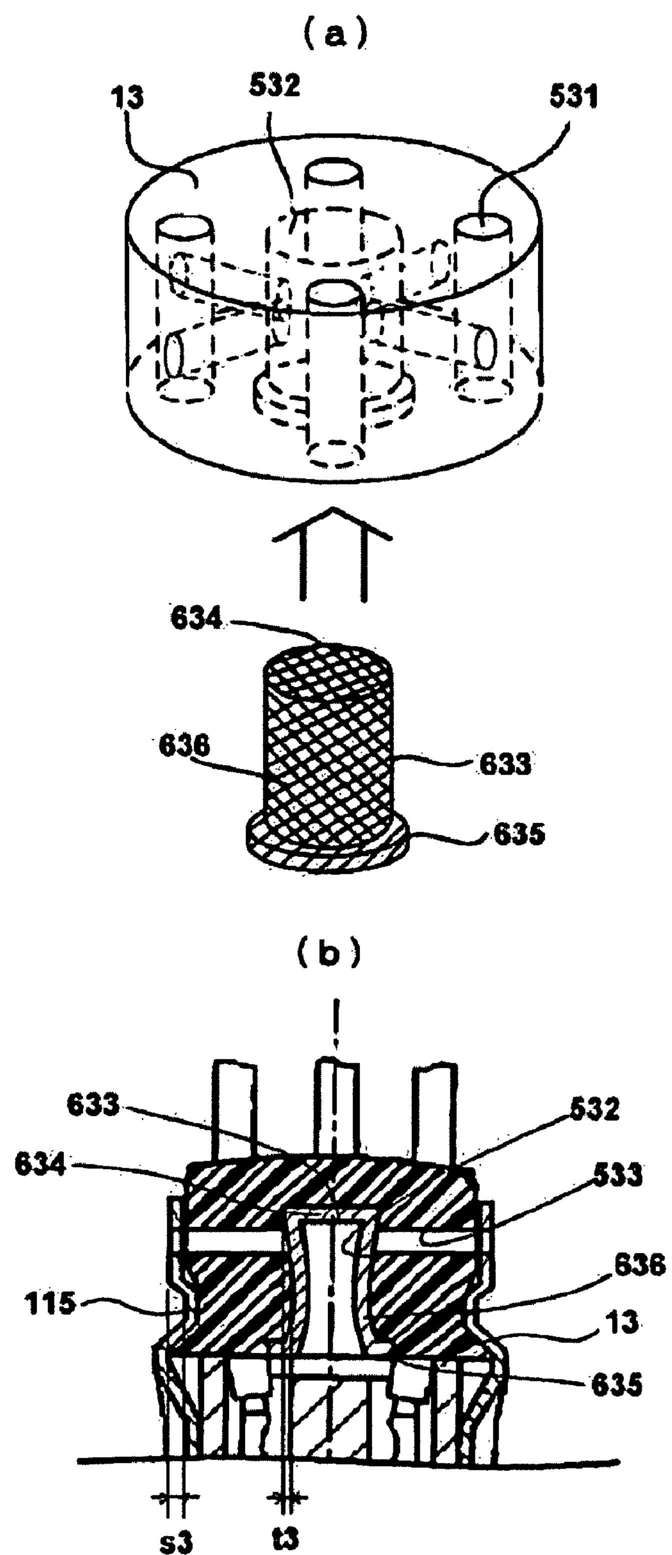
FIG. 7(*a*) is an exploded view of the region near the seal member in another embodiment, and (*b*) is a partial cross-sectional view of the region near the seal member in this embodiment.

A further embodiment will be described, using FIG. 7. In the above embodiments, a sheet-shaped metallic filter 133 was jointed to the hollow-cylindrical member 134 so as to block the atmosphere-introduction hole 132 extending in the axial direction. In contrast, in this embodiment, a metallic filter 633 is disposed with respect to an axial-direction communicating hole 532 that extends in the axial direction and a radial-direction communicating hole 533 that extends in the radial direction. The region near the seal member 13, which differs from the above embodiments, will be described, with the descriptions of other parts either omitted or simplified. FIG. 7(*a*) is an exploded view when the metallic filter 633 is inserted into the seal member 13, and FIG. 7(*b*) is a partial cross-sectional view when the metallic filter 633 is inserted into the seal member 13 and the seal member 13 is held by crimping of the outer tube 11.

As shown in FIG. 7, the axial-direction communicating hole 532 is provided at substantially the center of the seal member 13, and also a radial-direction communicating hole 533 is formed so as to join the outer peripheral surface of the seal member 13 and the axial-direction communicating hole 532. By the axial-direction communicating hole 532 and the radial-direction communicating hole 533, the front outer surface of the seal member 13 and the outer peripheral surface are linked. The metallic filter 633 is disposed inside the axial-direction communicating hole 532. The metallic filter 633 has a hollow-cylindrical part 636 that makes contact with the inner peripheral surface of the axial-direction communicating hole 532 of the seal member 13, a restricting part 635 provided on the front end of the hollow-cylindrical part that mates with a depression provided on the front end face of the seal member, and a cover part 634 provided on the rear end of the hollow-cylindrical part. Of these, part of the hollow-cylindrical part 636 is disposed so as to block the radial-direction communicating hole 533.

Additionally, the deformation amount t3 of the metallic filter 633 is 15% of the deformation amount s3 of the crimped part 115. By making the deformation amount t3 of the metallic filter 337 be at least 1% but no more than 50% of the deformation amount s3 of the crimped part 115 in this manner, when the seal member 13 is held by crimping of the outer tube 11, it is possible to limit to the minimum the effect on the metallic filter 633 of the compression force from the seal member 13, and possible to achieve sufficient ventilation in the metallic filter 633.

Although the foregoing has been a description of embodiments of the present invention, these do not restrict the present invention to the embodiments, and the present invention can be subjected to diverse design changes.

Figure 8:
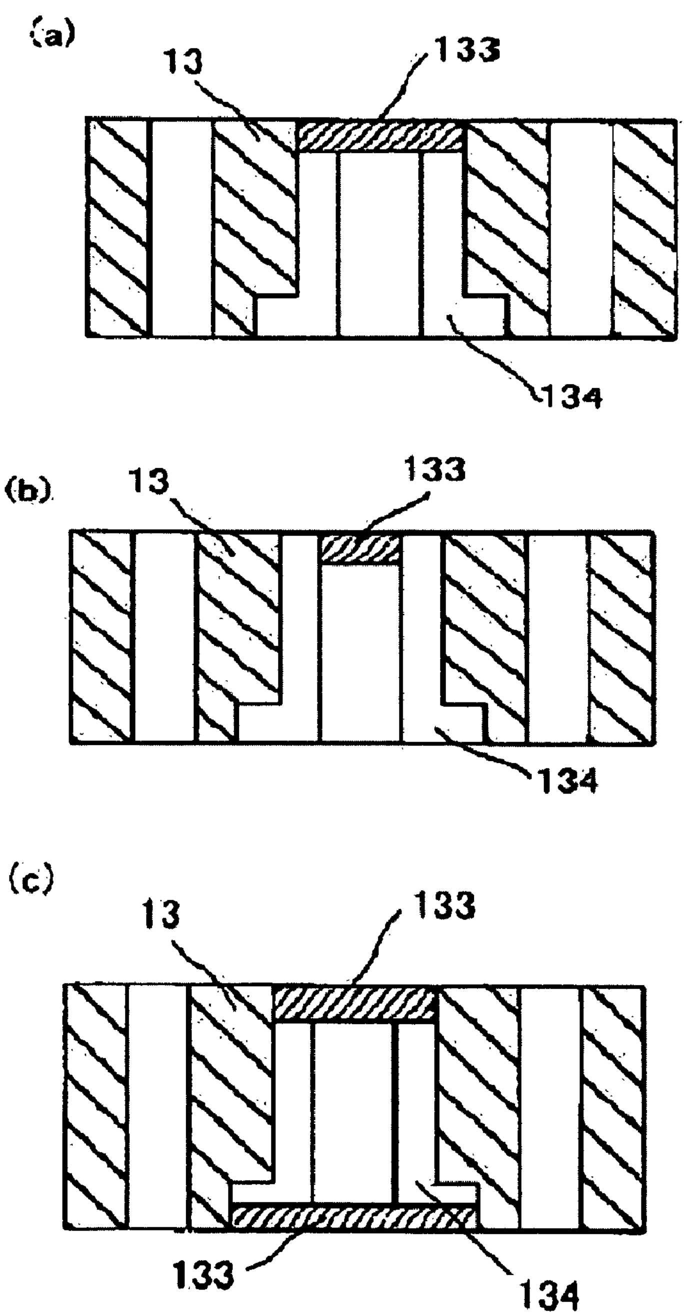
FIG. 8(*a*) is an assembly drawing of the region near the seal member before crimping, (*b*) is an assembly of the region near the seal member before crimping, and (*c*) is an assembly drawing of the region near the seal member before crimping.

For example, in the above embodiments, although the hollow-cylindrical part 136, and the restricting part 135 of the hollow-cylindrical member 134 are formed from different materials, the hollow-cylindrical part 136 and the restricting part 135 of the hollow-cylindrical member 134 may be formed from a single metallic material, shown in FIG. 8(*a*).

Also, whereas in the above embodiments the metallic filter is welded to the rear end of the hollow-cylindrical member 134, the metallic filter 133 may be welded to the rear end inner peripheral surface of the hollow-cylindrical member 134, as shown in FIG. 8(*b*).

Also, whereas in the above embodiments the number of metallic filters 133 welded to the hollow-cylindrical member 134 was one sheet, metallic filters 133 may each be welded to the trailing edge of the hollow-cylindrical member 134 and the leading edge of the hollow-cylindrical member 134 as shown in FIG. 8(*c*).

Also, whereas in the above embodiments the hollow-cylindrical member 134 and the metallic filter 133 are welded, there is no restriction to this, and it is possible, after disposing the metallic filter 133 in the hollow-cylindrical member 134, to join them together by soldering, brazing, or simultaneously sintering the joining surfaces between the metallic filter 133 and the hollow-cylindrical member 134. Also, whereas in an embodiment the hollow-cylindrical member 234 and the metallic filter 233 are joined together by simultaneous sintering, there is no restriction to this, and they may be joined together by brazing.

Additionally, although in some embodiments a metallic filter that has been treated for water repellency by glazing, and a metallic hollow-cylindrical member are used, these elements can respectively be a ceramic filter and a ceramic hollow-cylindrical member that have been treated for water repellency.

The invention claimed is:

1. A gas sensor comprising:
- a detection element, extending in the axial direction, that detects a particular gas component in a gas under measurement;
- a casing surrounding a periphery of the detection element and having a front end from which a front end of the detection element protrudes so that the front end of the detection element is exposed to the gas under measurement;
- a seal member disposed on a rear side with respect to the detection element and also inside the rear end of the casing, the seal member having a ventilation hole penetrating therethrough in the axial direction;
- a crimped part of the casing holding the seal member;
- a hollow-cylindrical member being in contact with an inner peripheral surface of the ventilation hole and being located opposed to and being held in place by the crimped part; and
- at least one of a metallic filter or a ceramic filter that joins to the hollow-cylindrical member at a base end of the hollow-cylindrical member and on a rear end side with respect to the crimped part, and that at least covers the ventilation hole, wherein said metallic filter or ceramic filter is coated with a water repellent material.

2. The gas sensor as claimed in claim 1, wherein the at least one of the metallic filter or the ceramic filter is sheet-shaped.

3. The gas sensor as claimed in claim 1, wherein the ceramic filter is disposed in the seal member, and wherein a glaze layer is formed on at least a side surface of the ceramic filter.

4. The gas sensor as claimed in claim 1, wherein the metallic filter is made of metallic materials selected from the group consisting of stainless steel, copper, copper alloy, nickel, low alloy steel, and aluminum.

5. The gas sensor as claimed in claim 4, wherein the metallic filter is made of stainless steel.

6. The gas sensor as claimed in claim 1, wherein the water repellent material is a fluorine-based resin.

7. A gas sensor comprising:
- a detection element, extending in the axial direction, that detects a particular gas component in a gas under measurement;
- a casing surrounding a periphery of the detection element and having a front end from which a front end of the detection element protrudes so that the front end of the detection element is exposed to the gas under measurement;
- a seal member disposed on a rear side with respect to the detection element and also inside a rear end of the casing, the seal member having a ventilation hole, from one outside surface toward another outside surface;
- a crimped part of the casing holding the seal member; and
- at least one of a metallic filter or a ceramic filter being in contact with an inner peripheral surface of the ventilation hole opposite the crimped part and being held by the crimped part, said filter at least covers the ventilation hole and is coated with a water repellent material,
- wherein a deformation amount of the at least one of the metallic filter or the ceramic filter is from 1% to 50% of a deformation amount of the crimped part.

8. The gas sensor as claimed in claim 7, wherein the ventilation hole extends in the axial direction from a front end surface of the seal member toward a rear end surface, and wherein the metallic filter or the ceramic filter comprises a covering part covering the ventilation hole and a hollow-cylindrical part connected to the covering part, the hollow-cylindrical part being in contact with the inner peripheral surface of the ventilation hole.

9. The gas sensor as claimed in claim 7, wherein the ventilation hole extends in the axial direction from a front end surface of the seal member toward a rear end surface, and wherein the at least one of the metallic filter or the ceramic filter comprises a rod shape that fills the ventilation hole and blocks the ventilation hole.

10. The gas sensor as claimed in claim 7, wherein the ventilation hole comprises:
- an axial-direction communicating hole that extends rearward from a front end surface of the seal member in the axial direction; and
- a radial-direction communicating hole that extends from an outer peripheral surface of the seal member to the axial-direction communicating hole, allowing communication from the front end surface of the seal member to the outer peripheral surface of the seal member,
- wherein the at least one of the metallic filter or the ceramic filter blocks the radial-direction communicating hole and is in contact with the inner peripheral surface of the axial-direction communicating hole.

11. The gas sensor as claimed in claim 7, wherein the ceramic filter is disposed in the seal member, and wherein a glaze layer is formed on at least a side surface of the ceramic filter.

12. The gas sensor as claimed in claim 7, wherein the metallic filter is made of metallic materials selected from the group consisting of stainless steel, copper, copper alloy, nickel, low alloy steel, and aluminum.

13. The gas sensor as claimed in claim 12, wherein the metallic filter is made of stainless steel.

14. The gas sensor as claimed in claim 7, wherein the water repellent material is a fluorine-based resin.

* * * * *